(12) United States Patent
Gram et al.

(10) Patent No.: US 7,491,392 B2
(45) Date of Patent: Feb. 17, 2009

(54) ANTIBODIES TO HUMAN IL-1β

(75) Inventors: Hermann Gram, Weil (DE); Franco E Di Padova, Birsfelden (CH)

(73) Assignee: Novartis AG, Basel (CH)

( * ) Notice: Subject to any disclaimer, the term of this patent is extended or adjusted under 35 U.S.C. 154(b) by 143 days.

(21) Appl. No.: 11/484,472

(22) Filed: Jul. 11, 2006

(65) Prior Publication Data

US 2006/0251660 A1 Nov. 9, 2006

Related U.S. Application Data (63) Continuation of application No. 10/181,324, filed as application No. PCT/EP01/00591 on Jan. 19, 2001, now abandoned.

(30) Foreign Application Priority Data

Jan. 21, 2000 (GB) .................................. 0001448.0

(51) Int. Cl.
*A61K 39/40* (2006.01)
*C07K 16/00* (2006.01)

(52) U.S. Cl. ............... 424/139.1; 530/387.1; 530/387.9

(58) Field of Classification Search ........................ None
See application file for complete search history.

(56) References Cited

U.S. PATENT DOCUMENTS 4,935,343 A 6/1990 Allison et al. .................. 435/7
6,632,927 B2 10/2003 Adair et al. .............. 530/387.3

FOREIGN PATENT DOCUMENTS

| EP | 0 218 531 | 10/1986 |
|---|---|---|
| EP | 0 491 031 | 7/1991 |
| WO | 90/06371 | 12/1989 |
| WO | 91/09967 | 12/1990 |
| WO | 95/01197 | 7/1994 |
| WO | 95 01997 | 1/1995 |
| WO | 99/42075 | 2/1999 |

OTHER PUBLICATIONS

Knappik et al., Journal of Molecular Biology, 2000, V.1 p. 57-86.*
Pascalis et al. The Journal of Immunology (2002) 169, 3076-3084.*
Matsuda et al., "The Complete Nucleotide Sequence of the Human Immunoglobulin Heavy Chain Variable Region Locus", J. Exp. Med., vol. 188, No. 11, pp. 2151-2162, (Dec. 7, 1998).
Le Xiaozhong, "Current Protocols of Biotechnology", Beijing Normal University Press, line 15 p. 256, line 10 p. 257, (1999).
Massone et al, "Mapping of Biologically Relevant Sites on Human Il-1Beta Using Monoclonal Antibodies", The Journal of Immunology, vol. 140, No. 11, pp. 3812-3816 (1988).
Simon et al, "Mapping of Neutralizing Epitopes and the Receptor Binding Site of Human Interleukin 1Beta*" The Journal of Biological Chemistry, vol. 268, No. 13, pp. 9771-9779 (1993).
Herzbeck et al., "Functional and Molecular Characterization of a Monoclonal Antibody Against the 165-186 Peptide of Human IL-1Beta", Scand. J. Immunol., vol. 30, pp. 549-562, (1989).
Paul, Fundamental Immunology, 1999, oo.37, 43, 58, 59.
Rudikoff et al., Proc Natl Acad Sci USA, 1982, vol. 79, p. 1979.
Panka et al., Proc Natl Acad Sci USA, vol. 85, 3080-3084, May, 1988.
Colman et al., Research in Immunology, (145(1):33-36, 1994.

* cited by examiner

*Primary Examiner*—Michail A Belyavskyi
(74) *Attorney, Agent, or Firm*—Leslie Fischer; Peter J. Waibel; Cozette M. McAvoy (57) ABSTRACT

An IL-1β binding molecule, in particular an antibody to human IL-1β, especially a human antibody to human IL-1β is provided, wherein the CDRs of the heavy and light chains have amino acid sequences as defined, for use in the treatment of an IL-1 mediated disease or disorder, e.g. osteoarthritis, osteoporosis and other inflammatory arthritides.

13 Claims, 3 Drawing Sheets

SEQUENCE LISTING

<160> NUMBER OF SEQ ID NOS: 4

<210> SEQ ID NO 1
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 1

```
gag gtg cag ctg gtg cag tct gga gca gag gtg aaa aag ccc ggg gag        48
Glu Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac        96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg       144
Trp Ile Gly Trp Val Arg Gln Met Pro Gly Lys Gly Leu Glu Trp Met
        35                  40                  45 ggg atc atc tat cct agt gac tct gat acc aga tac agc ccg tcc ttc       192
Gly Ile Ile Tyr Pro Ser Asp Ser Asp Thr Arg Tyr Ser Pro Ser Phe
    50                  55                  60 caa ggc cag gtc acc atc tca gcc gac aag tcc atc agc acc gcc tac       240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt       288
Leu Gln Trp Ser Ser Leu Lys Ala Ser Asp Thr Ala Met Tyr Tyr Cys
                85                  90                  95 gcg aga tat acc aac tgg gat gct ttt gat atc tgg ggc caa ggg aca       336
Ala Arg Tyr Thr Asn Trp Asp Ala Phe Asp Ile Trp Gly Gln Gly Thr
            100                 105                 110 atg gtc acc gtc tct tca                                                354
Met Val Thr Val Ser Ser
        115
```

<210> SEQ ID NO 2
<211> LENGTH: 118

```
<212> TYPE: PRT
<213> ORGANISM: Mus musculus

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Ser Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Thr Asn Trp Asp Ala Phe Asp Ile Trp Gly Gln Gly Thr
                100                 105                 110

Met Val Thr Val Ser Ser
            115

<210> SEQ ID NO 3
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 3 gaa att gtg ttg aca cag tct cca gcc acc ctg tct ttg tct cca ggg        48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac        96
Glu Arg Ala Thr Leu Ser Cys Arg Ala Ser Gln Ser Val Ser Ser Tyr
                20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
            35                  40                  45 tat gat gca tcc aac agg gcc act ggc atc cca gcc agg ttc agt ggc       192
Tyr Asp Ala Ser Asn Arg Ala Thr Gly Ile Pro Ala Arg Phe Ser Gly
        50                  55                  60 agt ggg tct ggg aca gac ttc act ctc acc atc agc agc ctt gag cct       240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg atg ttc       288
Glu Asp Phe Ala Val Tyr Tyr Cys Gln Gln Arg Ser Asn Trp Met Phe
                85                  90                  95 cct ttt ggc cag ggg acc aag ctg gag atc aaa                           321
Pro Phe Gly Gln Gly Thr Lys Leu Glu Ile Lys
                100                 105

<210> SEQ ID NO 4
<211> LENGTH: 107
<212> TYPE: PRT
<213> ORGANISM: Mus musculus

<400> SEQUENCE: 4

Glu Ile Val Leu Thr Gln Ser Pro Ala Thr Leu Ser Leu Ser Pro Gly
1               5                   10                  15
```

-continued

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Phe
                85                  90                  95

Pro Phe Gly Gln Gly Thr Lys Leu Glu Ile Lys
            100                 105
```

ANTIBODIES TO HUMAN IL-1β

This is a continuation of application Ser. No. 10/181,324 filed on Jul. 16, 2002, now abandoned, which is a 371 of International Application No. PCT/EP01/00591 filed on Jan. 19, 2001, which claims benefit of Great Britain Application No. 0001448.0 filed on Jan. 21, 2000, the entire disclosures of which are hereby incorporated by reference.

This invention relates to antibodies to human interleukin I beta (IL-1β) and to the use of such antibodies for the treatment of IL-1 mediated diseases and disorders.

Interleukin 1 (IL-1) is an activity produced by cells of the immune system which acts as a mediator of the acute phase inflammatory response. Inappropriate or excessive production of IL-1, in particular IL-1β, is associated with the pathology of various diseases and disorders, such as septicemia, septic or endotoxic shock, allergies, asthma, bone loss, ischemia, stroke, rheumatoid arthritis and other inflammatory disorders. Antibodies to IL-1β have been proposed for use in the treatment of IL-1 mediated diseases and disorders; see for instance, WO 95/01997 and the discussion in the introduction thereof.

We have now prepared improved antibodies to human IL-1β for use in the treatment of IL-1 mediated diseases and disorders.

Accordingly the invention provides an IL-1.beta. binding molecule which comprises an antigen binding site comprising at least one immunoglobulin heavy chain variable domain (V.sub.H) which comprises in sequence hypervariable regions CDR1, CDR2 and CDR3, said CDR1 having the amino acid sequence Ser-Tyr-Trp-Ile-Gly (SEQ ID NO:5), said CDR2 having the amino acid sequence Ile-Ile-Tyr-Pro-Ser-Asp-Ser-Asp-Thr-Arg-Tyr-Ser-Pro-Ser-Phe-Gln-Gly (SEQ ID NO:6)and said CDR3 having the amino acid sequence Tyr-Thr-Asn-Trp-Asp-Ala-Phe-Asp-Ile (SEQ ID NO:7); and direct equivalents thereof.

In a first aspect the invention provides a single domain IL-1β binding molecule comprising an isolated immunoglobulin heavy chain comprising a heavy chain variable domain ($V_H$) as defined above.

In a second aspect the invention also provides an IL-1β binding molecule comprising both heavy ($V_H$) and light chain ($V_L$) variable domains in which said IL-1β binding molecule comprises at least one antigen binding site comprising:

a) an immunoglobulin heavy chain variable domain (V.sub.H) which comprises in sequence hypervariable regions CDR1, CDR2 and CDR3, said CDR1 having the amino acid sequence Ser-Tyr-Trp-Ile-Gly (SEQ ID NO:5), said CDR2 having the amino acid sequence Ile-Ile-Tyr-Pro-Ser-Asp-Ser-Asp-Thr-Arg-Tyr-Ser-Pro-Ser-Phe-Gln-Gly, (SEQ ID NO:6), and said CDR3 having the amino acid sequence Tyr-Thr-Asn-Trp-Asp-Ala-Phe-Asp-Ile (SEQ ID NO:7), and b) an immunoglobulin light chain variable domain (V.sub.L) which comprises a CDR3' hypervariable region having the amino acid sequence Gln-Gln-Arg-Ser-Asn-Trp-Met-Phe-Pro (SEQ ID NO:10);

and direct equivalents thereof.

In particular embodiments of the second aspect the invention provides an IL-1β binding molecule comprising both heavy ($V_H$) and light ($V_L$) chain variable domains in which said IL-1β binding molecule comprises at least one antigen binding site comprising:

a) an immunoglobulin heavy chain variable domain (V.sub.H) which comprises in sequence hypervariable regions CDR1, CDR2 and CDR3, said CDR1 having the amino acid sequence Ser-Tyr-Trp-Ile-Gly (SEQ ID NO:5), said CDR2 having the amino acid sequence Ile-Ile-Tyr-Pro-Ser-Asp-Ser-AspThr-Arg-Tyr-Ser-Pro-Ser-Phe-Gln-Gly (SEQ ID NO:6), and said CDR3 having the amino acid sequence Tyr-Thr-Asn-Trp-Asp-Ala-Phe-Asp-Ile (SEQ ID NO:7), and b) an immunoglobulin light chain variable domain (V.sub.L) which comprises in sequence hypervariable regions CDR1', CDR2' and CDR3', said CDR1' having the amino acid sequence Arg-Ala-Ser-Gln-Ser-Val-Ser-Ser-Tyr-Leu Ala (SEQ ID NO:8), said CDR2' having the amino acid sequence Asp-Ala-Ser-Asn-Arg-Ala-Thr (SEQ ID NO:9), and said CDR3' having the amino acid sequence Gln-Gln-Arg-Ser-Asn-Trp-Met-Phe-Pro (SEQ ID NO:10);

and direct equivalents thereof.

Unless otherwise indicated, any polypeptide chain is herein described as having an amino acid sequence starting at the N-terminal extremity and ending at the C-terminal extremity. When the antigen binding site comprises both the $V_H$ and $V_L$ domains, these may be located on the same polypeptide molecule or, preferably, each domain may be on a different chain, the $V_H$ domain being part of an immunoglobulin heavy chain or fragment thereof and the $V_L$ being part of an immunoglobulin light chain or fragment thereof.

By "IL-1β binding molecule" is meant any molecule capable of binding to the IL-1β antigen either alone or associated with other molecules. The binding reaction may be shown by standard methods (qualitative assays) including, for example, a bioassay for determining the inhibition of IL-1β binding to its receptor or any kind of binding assays, with reference to a negative control test in which an antibody of unrelated specificity but of the same isotype, e.g. an anti-CD25 antibody, is used. Advantageously, the binding of the IL-1β binding molecules of the invention to IL-1β may be shown in a competitive binding assay.

Examples of antigen binding molecules include antibodies as produced by B-cells or hybridomas and chimeric, CDR-grafted or human antibodies or any fragment thereof, e.g. $F(ab')_2$ and Fab fragments, as well as single chain or single domain antibodies.

A single chain antibody consists of the variable domains of the heavy and light chains of an antibody covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin or of human origin but derived from a different human antibody. By "CDR-grafted antibody" is meant an antibody in which the hypervariable regions (CDRs) are derived from a donor antibody, such as a non-human (e.g. murine) antibody or a different human antibody, while all or substantially all the other parts of the immunoglobulin e.g. the constant regions and the highly conserved parts of the variable domains, i.e. the framework regions, are derived from an acceptor antibody, e.g. an antibody of human origin. A CDR-grafted antibody may however contain a few amino acids of the donor sequence in the framework regions, for instance in the parts of the framework regions adjacent to the hypervariable regions. By "human antibody" is meant an antibody in which the constant and variable regions of both the heavy and light chains are all of human origin, or substantially identical to sequences of human origin, not necessarily from the same antibody and includes antibodies produced by mice in which the murine immunoglobulin variable and constant part genes have been replaced by their human counterparts, e.g. as described in general terms in EP 0546073 B1, U.S. Pat. Nos. 5,545,806, 5,569,825, 5,625,126, 5,633,425, 5,661,016, 5,770,429, EP 0 438474 B1 and EP 0 463151 B1.

Particularly preferred IL-1β binding molecules of the invention are human antibodies especially the AAL 160 antibody as hereinafter described in the Examples.

Thus in preferred chimeric antibodies the variable domains of both heavy and light chains are of human origin, for instance those of the AAL 160 antibody which are shown in SEQ ID NO:1 and SEQ ID NO:2. Nucleic acid sequences for the $V_H$ and $V_L$ claims are set forth in SEQ ID NO:3 and SEQ ID NO:4, respectively. The constant region domains preferably also comprise suitable human constant region domains, for instance as described in "Sequences of Proteins of Immunological Interest", Kabat E. A. et al, US Department of Health and Human Services, Public Health Service, National Institute of Health Hypervariable regions may be associated with any kind of framework regions, though preferably are of human origin. Suitable framework regions are described in Kabat E. A. et al, ibid. The preferred heavy chain framework is a human heavy chain framework, for instance that of the AAL 160 antibody which is shown in SEQ ID NO:1. It consists in sequence of FR1, FR2, FR3 and FR4 regions. In a similar manner, SEQ ID NO:2 shows the preferred AAL 160 light chain framework which consists, in sequence, of FR1', FR2', FR3' and FR4' regions.

Accordingly, the invention also provides an IL-1.beta. binding molecule which comprises at least one antigen binding site comprising either a first domain having an amino acid sequence substantially identical to that shown in SEQ ID NO:1 starting with amino acid at position 1 and ending with amino acid at position 118 or a first domain as described above and a second domain having an amino acid sequence substantially identical to that shown in SEQ ID NO:2, starting with amino acid at position 1 and ending with amino acid at position 107.

Monoclonal antibodies raised against a protein naturally found in all humans are typically developed in a non-human system e.g. in mice. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric, CDR-grafted, or especially human antibodies which are not likely to elicit a substantial allogenic response when administered to humans.

In view of the foregoing, a more preferred IL-1β binding molecule of the invention is selected from a human anti IL-1β antibody which comprises at least a) an immunoglobulin heavy chain or fragment thereof which comprises (i) a variable domain comprising in sequence the hypervariable regions CDR1, CDR2 and CDR3 and (ii) the constant part or fragment thereof of a human heavy chain; said CDR1 having the amino acid sequence Ser-Tyr-Trp-Ile-Gly (SEQ ID NO:5), said CDR2 having the amino acid sequence Ile-Ile-Tyr-Pro-Ser-Asp-Ser-Asp-Thr-Arg-Tyr-Ser-Pro-Ser-Phe-Gln-Gly SEQ ID NO:6), and said CDR3 having the amino acid sequence Tyr-Thr-Asn-Trp-Asp-Ala-Phe-Asp-Ile (SEQ ID NO:7) and b) an immunoglobulin light chain or fragment thereof which comprises (i) a variable domain comprising the CDR3' hypervariable region and optionally also the CDR 1', CDR2' hypervariable regions and (ii) the constant part or fragment thereof of a human light chain, said CDR1' having the amino acid sequence Arg-Ala-Ser-Gln-Ser-Val-Ser-Ser-Tyr-Leu Ala (SEQ ID NO:8), said CDR2' having the amino acid sequence Asp-Ala-Ser-Asn-Arg-Ala-Thr (SEQ ID NO:9), and said CDR3' having the amino acid sequence Gln-Gln-Arg-Ser-Asn-Trp-Met-Phe-Pro (SEQ ID NO:10);

and direct equivalents thereof.

Alternatively, an IL-1β binding molecule of the invention may be selected from a single chain binding molecule which comprises an antigen binding site comprising a) a first domain comprising in sequence the hypervariable regions CDR1, CDR2 and CDR3, said hypervariable regions having the amino acid sequences as shown in SEQ ID NO:1, b) A second domain comprising the hypervariable regions CDR3' and optionally CDR1' and CDR2', said hypervariable regions having the amino acid sequences as shown in SEQ ID NO:2 and c) a peptide linker which is bound either to the N-terminal extremity of the first domain and to the C-terminal extremity of the second domain or to the C-terminal extremity of the first domain and to the N-terminal extremity of second domain;

and direct equivalents thereof.

As it is well known, minor changes in an amino acid sequence such as deletion, addition or substitution of one, a few or even several amino acids may lead to an allelic form of the original protein which has substantially identical properties.

Thus, by the term "direct equivalents thereof" is meant either any single domain IL-1β binding molecule (molecule X).

(i) in which the hypervariable regions CDR1, CDR2 and CDR3 taken as a whole are at least 80% homologous, preferably at least 90% homologous, more preferably at least 95% homologous to the hypervariable regions as shown in SEQ ID NO:1 and, (ii) which is capable of inhibiting the binding of IL-1.beta. to its receptors substantially to the same extent as a reference molecule having framework regions identical to those of molecule X but having hypervariable regions CDR1, CDR2 and CDR3 identical to those shown in SEQ ID NO:1 or any IL-1.beta. binding molecule having at least two domains per binding site (molecule X')

(i) in which the hypervariable regions CDR1, CDR2, CDR3, CDR3' and optionally CDR1' and CDR2' taken as a whole are at least 80% homologous, preferably at least 90% homologous, more preferably at least 95% homologous, to the hypervariable regions as shown in SEQ ID NO:1 and 2 and (ii) which is capable of inhibiting the binding of IL-1.beta. to its receptors substantially to the same extent as a reference molecule having framework regions and constant parts identical to molecule X', but having hypervariable regions CDR1, CDR2, CDR3, and CDR3', and optionally CDR1' and CDR2', identical to those shown in SEQ ID NO:1 and 2.

In the present description amino acid sequences are at least 80% homologous to one another if they have at least 80% identical amino acid residues in a like position when the sequence are aligned optimally, gaps or insertions in the amino acid sequences being counted as non-identical residues.

The inhibition of the binding of IL-1β to its receptor may be conveniently tested in various assays including such assays are described hereinafter in the text. The IL-1β receptor used is preferably the IL-1β type 1 receptor. By the term "to the same extent" is meant that the reference and the equivalent molecules exhibit, on a statistical basis, essentially identical IL-1β binding inhibition curves in one of the assays referred to above.

For example, the assay used may be an assay of competitive inhibition of binding of IL-1β by soluble IL-1 receptors and the IL-1β binding molecules of the invention.

Most preferably, the human IL-1β antibody comprises at least a) one heavy chain which comprises a variable domain having an amino acid sequence substantially identical to that shown in SEQ ID NO:1 starting with the amino acid at position 1 and ending with the amino acid at position 118 and the constant part of a human heavy chain; and b) one light chain which comprises a variable domain having an amino acid sequence substantially identical to that shown in SEQ ID NO:2 starting with the amino acid at position 1 and ending with the amino acid at position 107 and the constant part of a human light chain.

The constant part of a human heavy chain may be of the $\gamma_1$, $\gamma_2$, $\gamma_3$, $\gamma_4$, $\mu$, $\alpha_1$, $\alpha_2$, $\delta$ or $\epsilon$ type, preferably of the $\gamma$ type, more preferably of the $\gamma_1$ type, whereas the constant part of a human light chain may be of the $\kappa$ or $\lambda$ type (which includes the $\lambda_1$, $\lambda_2$ and $\lambda_3$ subtypes) but is preferably of the $\kappa$ type. The amino acid sequences of all these constant parts are given in Kabat et al ibid.

An IL-1β binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided
(i) DNA molecules encoding a single domain IL-1β binding molecule, of the invention, a single chain IL-1β binding molecule of the invention, a heavy or light chain or fragments thereof of a IL-1β binding molecule of the invention and
(ii) the use of the DNA molecules of the invention for the production of a IL-1β binding molecule of the invention by recombinant means.

The present state of the art is such that the skilled worker in the art is able to synthesize the DNA molecules of the invention given the information provided herein i.e. the amino acid sequences of the hypervariable regions and the DNA sequences coding for them. A method for constructing a variable domain gene is for example described in EPA 239 400 and may be briefly summarized as follows: A gene encoding a variable domain of a MAb of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given in SEQ ID NO:1 or 2. These cassettes are provided with sticky ends so that they can be ligated at the junctions of the framework Furthermore, it is not necessary to have access to the mRNA from a producing hybridoma cell line in order to obtain a DNA construct coding for the IL-1β binding molecules of the invention. Thus PCT application WO 90/07861 gives full instructions for the production of an antibody by recombinant DNA techniques given only written information as to the nucleotide sequence of the gene. The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649.

In view of the foregoing no hybridoma or cell line deposit is necessary to comply with the criteria of sufficiency of description.

In a particular embodiment the invention includes first and second DNA constructs for the production of an IL-1β binding molecule as described below:

The first DNA construct encodes a heavy chain or fragment thereof and comprises a) a first part which encodes a variable domain comprising alternatively framework and hypervariable regions, said hypervariable regions being in sequence CDR1, CDR2 and CDR3 the amino acid sequences of which are shown in SEQ ID NO:1; this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a stop codon.

Preferably, this first part encodes a variable domain having an amino acid sequence substantially identical to the amino acid sequence as shown in SEQ ID NO:1 starting with the amino acid at position 1 and ending with the amino acid at position 118. More preferably the first part has the nucleotide sequence as shown in SEQ ID NO:1 starting with the nucleotide at position 1 and ending with the nucleotide at position 354. Also preferably, the second part encodes the constant part of a human heavy chain, more preferably the constant part of the human .gamma.1 chain. This second part may be a DNA fragment of genomic origin (comprising introns) or a cDNA fragment (without introns).

The second DNA construct encodes a light chain or fragment thereof and comprises a) a first part which encodes a variable domain comprising alternatively framework and hypervariable regions; said hypervariable regions being CDR3' and optionally CDR1' and CDR2', the amino acid sequences of which are shown in SEQ ID NO:2; this first part starting with a codon encoding the first amino acid of the variable domain and ending with a codon encoding the last amino acid of the variable domain, and b) a second part encoding a light chain constant part or fragment thereof which starts with a codon encoding the first amino acid of the constant part of the light chain and ends with a codon encoding the last amino acid of the constant part or fragment thereof followed by a stop codon.

Preferably, this first part encodes a variable domain having an amino acid sequence substantially identical to the amino acid sequence as shown in SEQ ID NO:2 starting with the amino acid at position 1 and ending with the amino acid at position 107. More preferably, the first part has the nucleotide sequence as shown in SEQ ID NO:2 starting with the nucleotide at position 1 and ending with the nucleotide at position 321. Also preferably the second part encodes the constant part of a human-light chain, more preferably the constant part of the human kappa chain.

The invention also includes IL-1.beta. binding molecules in which one or more of the residues of CDR1, CDR2, CDR3, CDR1, CDR2' or CDR3' are changed from the residues shown in SEQ ID NO:1 and SEQ ID NO:2 for instance by mutation e.g. site directed mutagenesis of the corresponding DNA sequences. The invention includes the DNA sequences coding for such changed IL-1.beta. binding molecules. In particular the invention includes IL-1.beta. binding molecules in which one or more residues of CDR1' or CDR2' have been changed from the residues shown in SEQ ID NO:2.

In the first and second DNA constructs, the first and second parts may be separated by an intron, and, an enhancer may be conveniently located in the intron between the first and second parts. The presence of such an enhancer which is transcribed but not translated, may assist in efficient transcription. In particular embodiments the first and second DNA constructs comprise the enhancer of a heavy chain gene advantageously of human origin.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene, or a cytomegalovirus (CMV) promoter, e.g. a human CMV promoter.

The desired antibody may be produced in a cell culture or in a transgenic animal. A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains are produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g. a myeloma, hybridoma or a normal immortalised B-cell, which conveniently does not express any endogenous antibody heavy or light chain.

For expression in mammalian cells it is preferred that the IL-1β binding molecule coding sequence is integrated into the host cell DNA within a locus which permits or favours high level expression of the IL-1β binding molecule. Cells in which the IL-1β binding molecule coding sequence is integrated into such favourable loci may be identified and selected on the basis of the levels of the IL-1β binding molecule which they express. Any suitable selectable marker may be used for preparation of host cells containing the IL-1β binding molecule coding sequence; for instance, a dhfr gene/methotrexate or equivalent selection system may be used. Preferred systems for expression of the IL-1β binding molecules of the invention include GS-based amplification/selection systems, such as those described in EP 0256055 B, EP 0323997 B and European patent application 89303964.4. Preferably also the vector may contain other sequences as desired to facilitate expression, processing and export of the expressed protein; for example, the vector may typically contain a leader sequence asoociated with the coding sequence.

In a further aspect of the invention there is provided a process for the product of an IL-1β binding molecule which comprises (i) culturing an organism which is transformed with an expression vector as defined above and (ii) recovering the IL-1β binding molecule from the culture.

In accordance with the present invention it has been found that the AAL160 antibody has binding specificity for the antigenic epitope of human IL-1β which includes the loop comprising residues, Gly 22, Pro 23, Tyr 24 and Glu 25 of mature human IL-1β. (Residues, Gly 22, Pro 23, Tyr 24 and Glu 25 of mature human IL-1β correspond to residues 138, 139, 140 and 141 respectively of the human IL-1β precursor.) This epitope appears to be outside the recognition site of the IL-1 receptor and it is therefore most surprising that antibodies to this eptitope, e.g. the AAL160 antibody, are capable of inhibiting the binding of IL-1β to its receptor. Antibodies, in particular chimeric and CDR-grafted antibodies and especially human antibodies, which have binding specificity for the antigenic epitope of mature human IL-1β which includes the loop comprising residues, Gly 22, Pro 23, Tyr 24 and Glu 25 and which are capable of inhibiting the binding of IL-1β to its receptor; and use of such antibodies for the treatment of IL-1 mediated diseases and disorders, are novel and are included within the scope of the present invention.

Thus in a further aspect the invention includes an antibody to IL-1β which has antigen binding specificity for an antigenic epitope of human IL-1β which includes the loop comprising residues Gly 22, Pro 23, Tyr 24 and Glu 25 of mature human IL-1β of mature human IL-1β and which is capable of inhibiting the binding of IL-1β to its receptor.

In yet further aspects the invention includes:
i) use of an antibody to IL-1β, which has antigen binding specificity for an antigenic epitope of mature human IL-1β which includes the loop comprising residues Gly 22, Pro 23, Tyr 24 and Glu 25 and which is capable of inhibiting the binding of IL-1β to its receptor, for the treatment of an IL-1 mediated disease or disorder;
ii) a method for the treatment of an IL-1 mediated disease or disorders in a patient which comprises administering to the patient an effective amount of an antibody to IL-1β, which has antigen binding specificity for an antigenic epitope of mature human IL-1β which includes the loop comprising residues Gly 22, Pro 23, Tyr 24 and Glu 25 and which is capable of inhibiting the binding of IL-1β to its receptor;
iii) a pharmaceutical composition comprising an antibody to IL-1β, which has antigen binding specificity for an antigenic epitope of mature human IL-1β which includes the loop comprising residues Gly 22, Pro 23, Tyr 24 and Glu 25 and which is capable of inhibiting the binding of IL-1β to its receptor, in combination with a pharmaceutically acceptable excipient, diluent or carrier; and iv) use of an antibody to IL-1β, which has antigen binding specificity for an antigenic epitope of mature human IL-1β which includes the loop comprising residues Gly 22, Pro 23, Tyr 24 and Glu 25 and which is capable of inhibiting the binding of IL-1β to its receptor, for the preparation of a medicament for the treatment of an IL-1 mediated disease or disorder.

For the purposes of the present description an antibody is "capable of inhibiting the binding of IL-1β" if the antibody is capable of inhibiting the binding of IL-1β to its receptor substantially to the same extent as the AAL160 antibody, wherein "to the same extent" has meaning as defined above.

In the present description the phrase "IL-1 mediated disease" encompasses all diseases and medical conditions in which IL-1 plays a role, whether directly or indirectly, in the disease or medical condition, including the causation, development, progress, persistence or pathology of the disease or condition.

In the present description the terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse.

Antibodies which have binding specificity for the antigenic epitope of mature human IL-1β which includes the loop comprising residues Gly 22, Pro 23, Tyr 24 and Glu 25 and which are capable of inhibiting the binding of IL-1β to its receptor are hereinafter referred to as Antibodies of the Invention. Preferably Antibodies of the Invention are antibodies which have binding specificity for this epitope of human IL-1β when the human IL-1β is under native, e.g. normal physiological conditions, not under denatured conditions, e.g. not in the presence of a denaturing agent such as SDS. Antibodies of the Invention may cross-react with non-human IL-1βs, which have antigenic epitopes which include Gly at residue 22, Pro at residue 23, Tyr at residue 24 and Glu at residue 25 and which are closely similar to the corresponding human epitope. For example, Antibodies of the Invention may cross-react with primate IL-1βs, such as rhesus monkey, cynomolgus monkey IL-1 or marmoset monkey IL-1.

Preferably the Antibodies of the Invention are IL-1β binding molecules according to the first and second aspects of the invention. Advantageously the Antibodies of the Invention are human antibodies, most preferably the AAL160 antibody or direct equivalent thereof.

The Antibodies of the Invention block the effects of IL-1β on its target cells and thus are indicated for use in the treatment of IL-1 mediated diseases and disorders. These and other pharmacological activities of the Antibodies of the Invention may be demonstrated in standard test methods for example as described below:

1. Neutralization of Human IL-1β-Mediated Activation of the IL-8 Promoter

The potential to neutralize IL-1β-dependent cellular signaling is determined in a reporter gene assay.

The human melanoma cell line G361 is stably transfected with a luciferase reporter gene construct based on the human IL-8 promoter. Reporter gene expression and activity is dependent on IL-1β or TNFα in this cell line. Cells are stimulated with 300 pg/ml of recombinant human IL-1β or the equivalent of 100 pg/ml in conditioned medium in the presence of various concentrations of Antibody of the Invention or IL-1 receptor antagonist ranging between 6 and 18,000 pM. The chimeric antibody Simulect® (basiliximab) is used as a matched isotype control. Luciferase activity is quantified in a chemiluminescence assay. Antibodies of the Invention typically have $IC_{50}$ of about 1 nM (e.g. from about 0.2 to about 5 nM) when tested in this assay.

2. Neutralization of IL-1β Dependent Production of $PGE_2$ and Interleukin-6 by Primary Human Fibroblasts The production of $PGE_2$ and IL-6 in primary human dermal fibroblasts is dependent on IL-1β. TNF-α alone cannot efficiently induce these inflammatory mediators, but synergizes with IL-1. Primary dermal fibroblasts are used as a surrogate model for IL-1-induced cellular activation.

Primary human fibroblasts are stimulated with recombinant IL-1β or conditioned medium obtained from LPS-stimulated human PBMCs in the presence of various concentrations of Antibody of the Invention or IL-1RA ranging from 6 to 18,000 pM. The chimeric anti-CD25 antibody Simulect® (basiliximab) is used as a matched isotype control. Supernatant is taken after 16 h stimulation and assayed for IL-6 by ELISA or $PGE_2$ by RIA. Antibodies of the Invention typically have $IC_{50}$s for inhibition of IL-6 production of about 1 nM or less (e.g. from about 0.1 to about 1 nM) and for inhibition of $PGE_2$ production of about 1 nM (e.g. from about 0.1 to about 1 nM) when tested as above.

As indicated in the above assays Antibodies of the Invention potently block the effects of IL-1β. Accordingly, the Antibodies of the Invention have pharmaceutical utility as follows:

Antibodies of the Invention are useful for the prophylaxis and treatment of IL-1 mediated diseases or medical conditions, e.g. inflammatory conditions, allergies and allergic conditions, hypersensitivity reactions, autoimmune diseases, severe infections, and organ or tissue transplant rejection.

For example, Antibodies of the Invention may be use for the treatment of recipients of heart, lung, combined heart-lung, liver, kidney, pancreatic, skin or corneal transplants and for the prevention of graft-versus-host disease, such as following bone marrow transplant.

Antibodies of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, hypersensitivity (including both airways hypersensitivity and dermal hypersensitivity) and allergies. Specific autoimmune diseases for which Antibodies of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Antibodies of the Invention are also useful for the treatment, prevention, or amelioration of asthma, bronchitis, pneumoconiosis, pulmonary emphysema, and other obstructive or inflammatory diseases of the airways Antibodies of the Invention are useful for treating undesirable acute and hyperacute inflammatory reactions which are mediated by IL-1 or involve IL-1 production, especially IL-1β, or the promotion of TNF release by IL-1, e.g. acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Antibodies of the Invention are particularly useful for treating diseases of bone metabolism including osteoarthritis, osteoporosis and other inflammatory arthritides, and bone loss in general including age-related bone loss, and in particular periodontal disease.

Antibodies of the Invention may be used for treatment of cancers, in particular IL-1-dependent tumours.

For these indications, the appropriate dosage will, of course, vary depending upon, for example, the particular Antibody of the Invention to be employed, the host, the mode of administration and the nature and severity of the condition being treated. However, in prophylactic use, satisfactory results are generally indicated to be obtained at daily dosages from about 0.1 mg to about 5 mg per kilogram body weight. Antibody of the Invention is conveniently administered parenterally, intravenously, e.g. into the antecubital or other peripheral vein, intramuscularly, or subcutaneously. A prophylactic treatment typically comprises administering the molecule of the invention once daily to once weekly for 2 to 4 weeks.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion, e.g. iv infusion, rather than as a bolus injection, e.g. a sc bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

The invention is further described by way of illustration only in the following Examples which refer to the accompanying Figures.

EXAMPLES

Transgenic mice engineered to express the human IgG/κ repertoire instead of the murine immunoglobulin repertoire (Fishwild et al., 1996, Nat Biotechnol., 14, 845-851) are used to generate antibodies to human IL-1β. B cells from these mice are immortalized by standard hybridoma technology and murine hybridoma cells are obtained which secrete the human IgG1/κ antibody AAL 160

Example 1

Generation of the Hybridoma and Purification of the Antibody

Genetically engineered mouse 66 (Medarex Inc. Annadale, N.J.) is immunized with recombinant human IL-1β (50 µg) s.c. in several sites in adjuvant. The mouse is boosted five additional times with the last injection three days before the fusion. On the day of the fusion mouse 66 is killed by $CO_2$ inhalation and spleen cells ($4.1 \times 10^7$) are fused by a routine method using PEG 4000 with an equal number of PAI-O cells, a mouse myeloma cell line. Fused cells are plated out in 624 wells (1 ml/well) containing a feeder layer of mouse peritoneal cells (Balb C mice), in HAT supplemented RPMI 1640, 10% heat inactivated fetal calf serum $5 \times 10^{-5}$ M β-mercaptoethanol. Supernatants are collected and tested in ELISA and screened for IL-1β reactive monoclonal antibodies. Five monoclonal antibodies of the IgG/κ subclass are identified. Cloning is done using 4×96 well microtiter plates, plating 0.5 cells per well. After two weeks wells are inspected with an inverted microscope. Supernatant is collected from wells positive for growth and production of anti-IL-1β monoclonal antibodies is evaluated by ELISA. 1-2 L of conditioned supernatant from four subclones of the originally identified hybridoma #476 are prepared and antibodies are purified by affinity chromatography on a protein A column.

Purity and Partial Amino Acid Sequences of Heavy and Light Chain

Amino Acid Sequencing

Light and heavy chains of the purified antibody AAL160 are separated by SDS-PAGE and the amino-terminal amino acids determined by Edman degradation. The purity of the antibody used in these studies is ≧90% by sequencing. cDNA sequences coding for the heavy and light chain variable domains are obtained by PCR amplification of cDNA obtained from mRNA from the cloned hybridoma cells and fully sequenced. The amino-terminal sequences of heavy and light chain variable domains and the corresponding DNA sequences are given below, in which the CDRs are shown in bold type.

```
                         30                              60        Seq. Id no. 1
GAG GTG CAG CTG GTG CAG TCT GGA GCA GAG GTG AAA AAG CCC GGG GAG TCT CTG AAG ATC
Glu Val Gln Leu Val Gln Ser Gly Ala Glu Val Lys Lys Pro Gly Glu Ser Leu Lys Ile
                         10                                                  20
                         90            CDR1                      120
TCC TGT AAG GGT TCT GGA TAC AGC TTT ACC AGC TAC TGG ATC GGC TGG GTG CGC CAG ATG
Ser Cys Lys Gly Ser Gly Tyr Ser Phe Thr Ser Tyr Trp Ile Gly Trp Val Arg Gln Met
                         30                                                  40
```

-continued

```
                              150        CDR2                             180
CCC GGG AAA GGC CTG GAG TGG ATG GGG ATC ATC TAT CCT AGT GAC TCT GAT ACC AGA TAC
Pro Gly Lys Gly Leu Glu Trp Met Gly Ile Ile Tyr Pro Ser Asp Ser Asp Thr Arg Tyr
                                          50                                60

210                                         240
AGC CCG TCC TTC CAA GGC CAG GTC ACC ATC TCA GCC GAC AAG TCC ATC AGC ACC GCC TAC
Ser Pro Ser Phe Gln Gly Gln Val Thr Ile Ser Ala Asp Lys Ser Ile Ser Thr Ala Tyr
                                          70                                80

270                                         300
CTG CAG TGG AGC AGC CTG AAG GCC TCG GAC ACC GCC ATG TAT TAC TGT GCG AGA TAT ACC
Leu Gln Trp Ser Ser Leu Lys Ala Ser Asp Thr Ala Met Tyr Tyr Cys Ala Arg Tyr Thr
                                          90                               100

CDR3                              330
AAC TGG GAT GCT TTT GAT ATC TGG GGC CAA GGG ACA ATG GTC ACC GTC TCT TCA
Asn Trp Asp Ala Phe Asp Ile Trp Gly Gln Gly Thr Met Val Thr Val Ser Ser 30                                         60   Seq. Id no. 2
GAA ATT GTG TTG ACA CAG TCT CCA GCC ACC CTG TCT TTG TCT CCA GGG GAA AGA GCC ACC
Glu Ile Val Leu Thr Gln Ser Pro Ala Thr Leu Ser Leu Ser Pro Gly Glu Arg Ala Thr
                              10                                          20

CDR1          90                                     120
CTC TCC TGC AGG GCC AGT CAG AGT GTT AGC AGC TAC TTA GCC TGG TAC CAA CAG AAA CCT
Leu Ser Cys Arg Ala Ser Gln Ser Val Ser Ser Tyr Leu Ala Trp Tyr Gln Gln Lys Pro
                                  30                                      40

150   CDR2                                  180
GGC CAG GCT CCC AGG CTC CTC ATC TAT GAT GCA TCC AAC AGG GCC ACT GGC ATC CCA GCC
Gly Gln Ala Pro Arg Leu Leu Ile Tyr Asp Ala Ser Asn Arg Ala Thr Gly Ile Pro Ala
                                          50                                60

210                                         240
AGG TTC AGT GGC AGT GGG TCT GGG ACA GAC TTC ACT CTC ACC ATC AGC AGC CTT GAG CCT
Arg Phe Ser Gly Ser Gly Ser Gly Thr Asp Phe Thr Leu Thr Ile Ser Ser Leu Glu Pro
                                          70                                80

270   CDR3                                  300
GAA GAT TTT GCA GTT TAT TAC TGT CAG CAG CGT AGC AAC TGG ATG TTC CCT TTT GGC CAG
Glu Asp Phe Ala Val Tyr Tyr Cys Gln Gln Arg Ser Asn Trp Met Phe Pro Phe Gly Gln
                                          90                               100

GGG ACC AAG CTG GAG ATC AAA
Gly Thr Lys Leu Glu Ile Lys
```

The DNA sequences coding for the heavy and light chain variable domains and the corresponding amino acid sequences of AAL160 are also give in the accompanying sequence listing as SEQ ID NOs:3 and 4.

Construction of Expression Vectors for Heavy and Light Chain

The cloned $V_L$ and $V_H$ encoding sequences were amplified by PCR and inserted via appropriate restriction sites into cassette vectors providing the immunoglobulin promoter, the leader sequences from the RFT2 antibody (Heinrich et al. (1989) J. Immunol. 143, 3589-97), part of the J-segments and a splice donor site. The light chain cassette containing the entire $V_L$ region, promoter and leader sequence for secretion was transferred into an expression vector containing the human Ck gene, the immunoglobin heavy chain enhancer, and the modified murine dhfr cDNA for selection by methotrexate (MTX).

The heavy chain cassette was transferred accordingly into an expression vector encoding the human IgG1 gene, the immunoglobulin heavy chain enhancer, and the neomycin resistance gene for selection.

Both heavy and light chain are in a configuration in the expression vectors that resembles the genomic configuration of rearranged immunoglobulin genes which is thought to be crucial for high level expression.

For Antibody production the above vectors are co-transfected into an appropriate host cell line, e.g. the SP2/0 cell line, cells containing the vector sequences are selected by methotrexate selection, and selected cell lines are cultured to express the AAL160 antibody. Alternatively a GS based amplification/selection system such as that described in EP 0256055 B, EP 0323997 B or European patent application 89303964.4 may be used, in which case the dhfr selectable marker is replaced by a GS coding sequence.

Example 2

Biochemical and Biological Data

The monoclonal antibody AAL160 is found to neutralize the activity of interleukin-1β in vitro. The monoclonal antibody is further characterized for its binding to recombinant human IL-1β Biacore analysis. The mode of neutralization is assessed by competitive binding studies with soluble IL-1 receptors. The biological activity of the antibody AAL160 towards recombinant and naturally produced IL-1β is determined in primary human cells (Example 3), responsive to stimulation by IL-1β.

2.1 Determination of Dissociation Equilibrium Constant

The association and dissociation rate constant for the binding of recombinant human IL-1β to AAL160 is determined by BIAcore analysis. AAL160 is immobilized, and binding of recombinant IL-1β in a concentration range from 0.5 to 12 nM is measured by surface plasmon resonance. The chosen format permits treating the binding event of IL-1β to AAL160 according to a 1:1 stoichiometry. Data analysis is performed using the BIAevaluation software.

| Association rate constant [M$^{-1}$s$^{-1}$] | (n = 15) | (3.91 ± 0.14) × 10$^5$ | Mean ± SEM |
|---|---|---|---|
| Dissociation rate constant [s$^{-1}$] | (n = 15) | (1.53 ± 0.05) × 10$^{-4}$ | Mean ± SEM |
| Dissociation equilibrium constant K$_D$ [M] | (n = 15) | (396.6 ± 19.5) × 10$^{-12}$ | Mean ± SEM |

AAL160 binds to recombinant human IL-1β with a high affinity.

2.2. Competitive Inhibition of Binding to Soluble IL-1 Receptors

Binding Competition Study with Soluble IL-1 Type I and II Receptors

Figure 1:
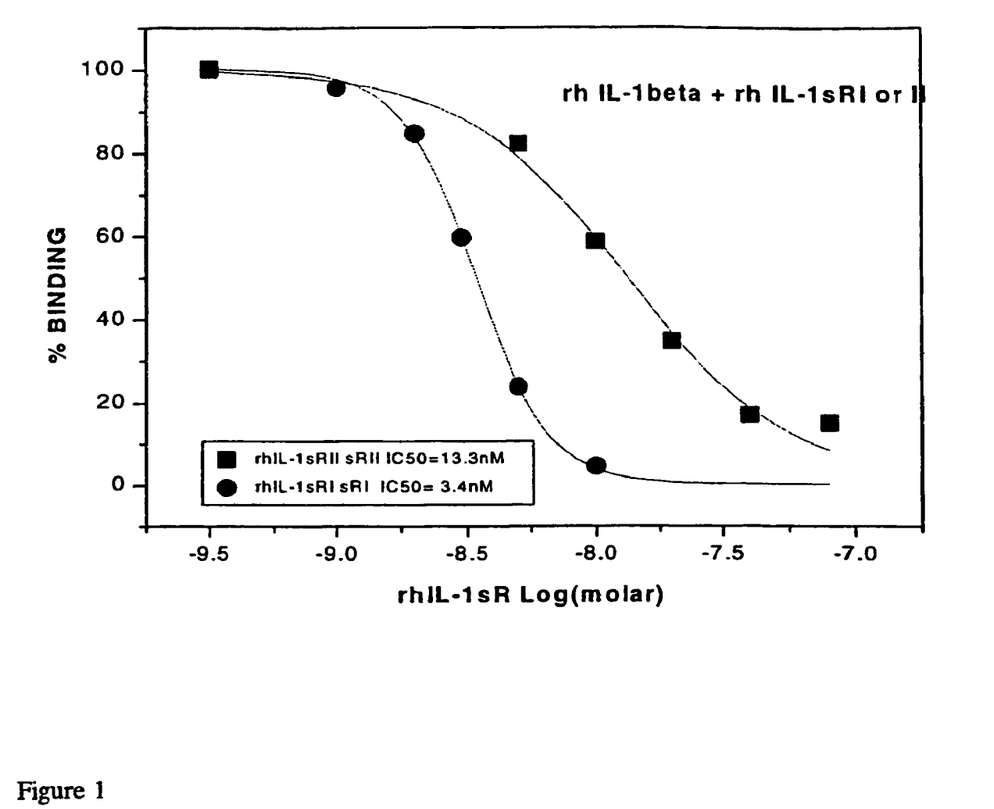
FIG. 1 which is a graph showing competitive inhibition of AAL160 binding to IL-1β by soluble IL-1 type I and type II receptors.

Competition between AAL160 and soluble human IL-1 type I and type II receptors is measured by Biacore. AAL160 is immobilized on the chip surface and recombinant human IL-1β (8 nM) is injected for binding to AAL160 in absence or presence of increasing concentrations of recombinant human soluble receptor I (0-10 nM) or receptor II (0-80 nM). The results obtained are shown in FIG. 1. Binding of NVP AAL160 NX-1 to IL-1β is competitive with both IL-1 receptor type I and type II 2.3. Reactivity Profile to Human IL-1α, Human IL-1RA, and IL-1β from Rodent and Monkey Species The reactivity profile of AAL160 to human IL-1α, IL-1RA, and murine, rat, rabbit and cynomolgus monkey IL-1β is determined by Biacore analysis. AAL160 is immobilized, and the cytokines examined are applied at a concentration of 8 nM (or 20 nM in the case of IL-1β.)

| | Percent of total binding ± SEM |
|---|---|
| Human IL-1β | 100 |
| Human IL-1α | 0.7 ± 0.7 (n = 3) |
| Human IL-1Ra | 1.2 ± 1.2 (n = 3) |
| Mouse IL-1β | 2.8 ± 1.5 (n = 3) |
| Rat IL-1β | 3.0 ± 2.5 (n = 3) |
| Cynomolgus IL-1β | 96.4 ± 6.8 (n = 3) |
| Rabbit IL-1β | 12.1 ± 2.3 (n = 4) |

AAL160 does not significantly crossreact with human IL-1α, human IL-1Ra, or murine, rat or rabbit IL-1β. The reactivity towards cynomolgus monkey IL-1β is virtually identical to the human cytokine.

Example 3

Neutralization of IL-1β-Dependent Production of PGE$_2$ and Interleukin-6 by Primary Human Fibroblasts The production of PGE$_2$ and IL-6 in primary human dermal fibroblasts is dependent on IL-1β. TNF-α alone cannot efficiently induce these inflammatory mediators, but synergizes with IL-1. Primary dermal fibroblasts are used as a surrogate model for IL-1 induced cellular activation.

Primary human fibroblasts are stimulated with recombinant IL-1β or conditioned medium obtained from LPS-stimulated human PBMCs in the presence of various concentrations of AAL160 or IL-1RA ranging from 6 to 18,000 pM. The chimeric anti-CD25 antibody Simulect® (basiliximab) is used as a matched isotype control. Supernatant is taken 16 hours after stimulation and is assayed for IL-6 by ELISA or PGE$_2$ by RIA.

| | AAL160 IC$_{50}$ ± SEM (n ≧ 3) | IL-1 Ra IC$_{50}$ ± SEM (n ≧ 3) |
|---|---|---|
| IL-6 secretion Recombinant | 0.34 ± 0.037 nM | n.d. |
| IL-6 secretion cond. Medium | 0.6 ± 0.09 nM | 0.03 ± 0.001 nM |
| PGE$_2$ production cond. Medium | 0.79 ± 0.17 nM | n.d. |

AAL160 effectively blocks production of IL-6 and PGE$_2$ in human dermal fibroblasts with an IC$_{50}$ similar for both the recombinant and natural IL-1β.

Example 4

In Vivo Efficacy and Duration of Action of AAL160

Figure 2:
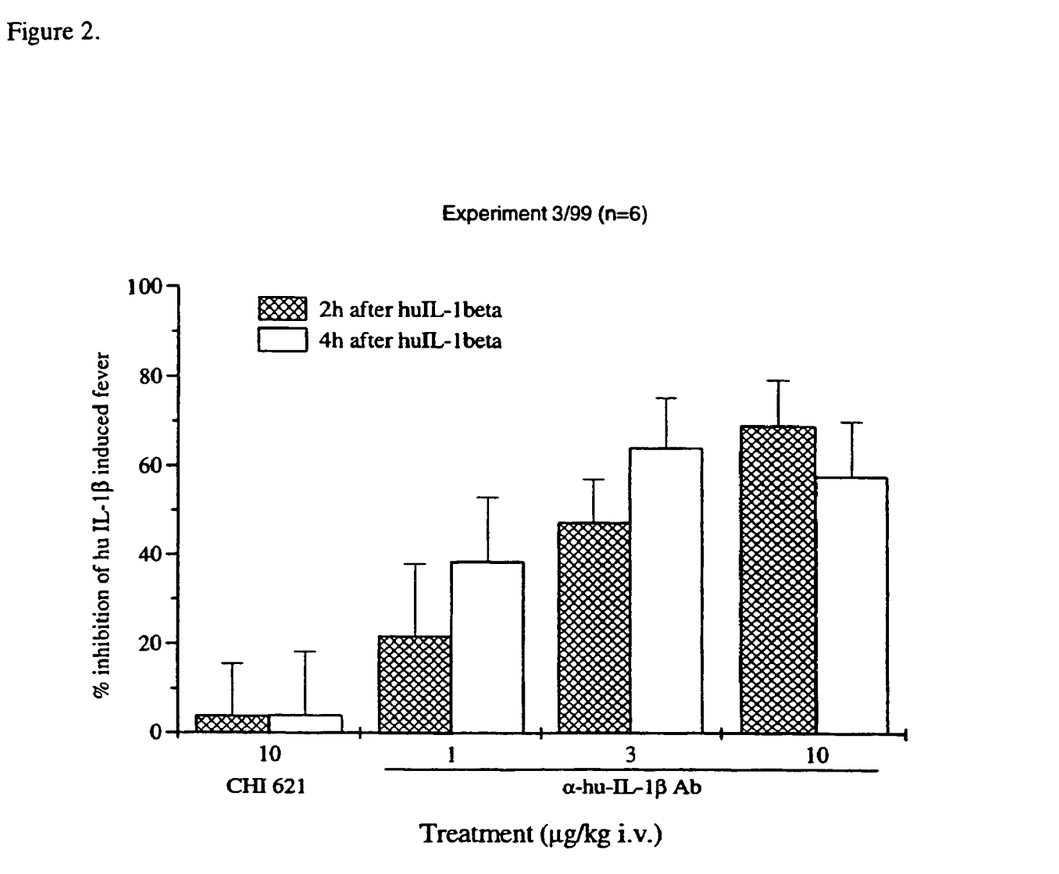
FIG. 2 which is a graph showing inhibition of IL-1β-induced fever in a rat model by AAL160, and FIG. 3 which is a graph showing duration of action of AAL160 in rat IL-1β-induced fever.

Efficacy:

The in vivo efficacy of the anti-huIL-1β antibody, AAL 160 is tested in a rat model where fever is induced by an i.v. injection of huIL-1β (100 ng/rat). The antibody causes a dose related inhibition of the fever response over the dose range 1, 3 and 10 μg/kg i.v. (n=6 rats)—see FIG. 2. CHI 621 (Simulect®, basiliximab) is used as the control antibody.

Figure 3:
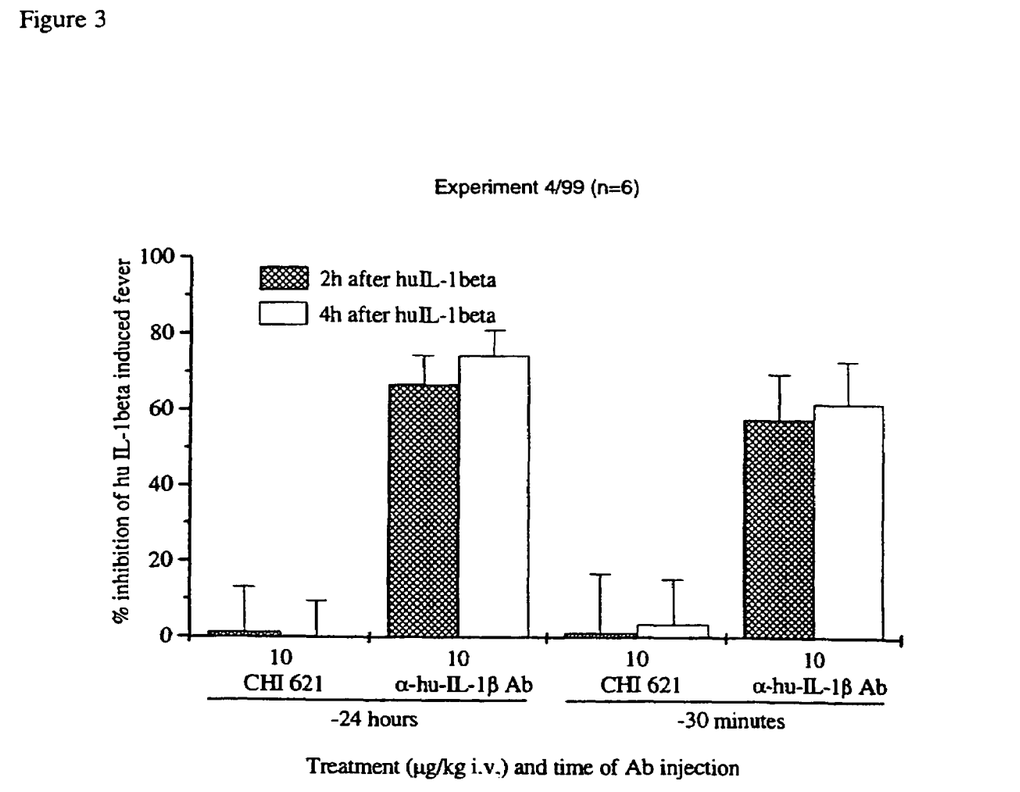

Duration of Action:

The duration of action of AAL-160 is investigated in rat IL-1β-induced fever as follows: The antibody is injected i.v. either 24 hours or 30 minutes (standard protocol) before the induction of fever by an i.v. injection of human IL-1β, and body temperature measured 2 and 4 hours later. A similar degree of inhibition of the fever response is seen at both times (see FIG. 3). As expected, the control antibody CHI 621 (Simulect®, basiliximab) is ineffective at both time-points. This finding indicates that the AAL160 human antibody is present in an active form for at least 24 hours in the rat and is not metabolised, excreted or bound in the tissues during this time.

Example 5

X-ray Studies of AAL160 Fab and its Complex with IL-1β Structure Determination of AAL160 Fab at 2.0 Å Resolution A 2.0 Å resolution data set of very good quality (R$_{sym}$=0, 051, completeness=99.9%, redundancy=8.2) was collected from an Fab crystal grown by the vapour diffusion in hanging drop technique, at pH 9.5 in 50% PEG 200, 0.1M CHES. The crystal was in space group P2$_1$2$_1$2$_1$ with unit cell dimensions a=62.17 Å b=89.83 Å c=123.73 Å and one Fab molecule per symmetric unit (Matthews coefficient: 3.6 Å$^3$/Da, estimated solvent content: 66%). The structure was determined by molecular replacement and was refined to a final crystallographic R-factor of 0.209 (free R-factor=0.261). The final model includes residues 1-213 of the light chain, 1-131 and 138-218 of the heavy chain, 387 water molecules and 1PEG molecule. The final electron density is well defined for all CDR residues but Trp 94 (CDR3) of the light chain. The position of the side-chain of this residue is ill defined in the two crystal forms which were examined to date, thus suggesting that it is highly mobile in the absence of a bound antigen.

Crystallization of the Fab complex with IL-1β and preliminary experimental model of the complex: a few crystals of AAL160 Fab in complex with the antigen IL-1β were obtained from a 76 mg/ml stock solution of the 1:1 complex in 2.0M ammonium sulfate, 0.1M Tris pH 8.5. The crystals grew very slowly over a period of several weeks. They diffracted weakly to about 3.2 Å on the home source. A preliminary data set was collected and molecular replacement was attempted using the high resolution structures of the free Fab and of human IL-1β (J. P. Priestle et al., EMBO J. 7, 339 (1988)) as starting models. The calculations yielded a very clear and unambiguous solution when the Fv and Fc parts of the Fab were used as separate modules (correlation 67.1%, R-factor 0.354 after the AMORE FITTING step, using data between 8.0 and 3.5 Å). The subsequent comparison of the free and bound forms of the Fab showed that the elbow angle is very different in the two structures. The results of the molecular replacement calculations provide a first molecular model of the interactions between the antigen IL-1β and the monoclonal antibody AAL160. A preliminary analysis of these interactions indicates that 1) IL-1β makes tight interactions to all three CDRs of the heavy chain and to CDR3 of the light chain. In contrast, few interactions if any involve CDR1 and CDR2 of the light chain. 2) The loop comprising residues Gly 22, Pro 23, Tyr 24 and Glu 25 of mature IL-1β binds at the centre of the antigen-combining site and thus appears to be a key component of the epitope. Interestingly enough, this loop is not located in the region of the molecule that differs most from mouse IL-1β. Pro 23, Tyr 24 and Glu 25 are conserved, but residue 22 is a Gly in human IL-1β and an Asp in mouse IL-1β. Comparison of the crystal structures of human (PDB entry 2i1b) and mouse IL-1β (PDB entry 8i1b) shows that this point mutation results in a very different conformation of the main-chain around Pro 23. This local structural difference is consistent with the observed lack of cross-reactivity of AAL160 with respect to the mouse cytokine.

The invention claimed is:

1. An isolated IL-1β binding molecule comprising a heavy chain variable domain comprising SEQ ID NO:1.

2. An isolated IL-1β binding molecule comprising a light chain variable domain comprising SEQ ID NO:2.

3. The isolated IL-1β binding molecule of claim 1, further comprising a light chain variable domain comprising SEQ ID NO:2.

4. The isolated IL-1β binding molecule of claim 2, further comprising a heavy chain variable domain comprising SEQ ID NO:1.

5. An isolated IL-1β binding molecule comprising a heavy chain variable domain comprising SEQ ID NO:1 and a light chain variable domain comprising SEQ ID NO:2.

6. An isolated IL-1β binding molecule comprising a heavy chain variable domain comprising the three CDRs of SEQ ID NO:1 and a light chain variable domain comprising the three CDRs of SEQ ID NO:2.

7. An isolated IL-1β binding molecule that is capable of inhibiting the binding of IL-1β to the IL-1β receptor to the same extent as an IL-1β binding molecule comprising a heavy chain variable domain comprising SEQ ID NO:1.

8. An isolated IL-1β binding molecule that is capable of inhibiting the binding of IL-1β to the IL-1β receptor to the same extent as an IL-1β binding molecule comprising a light chain variable domain comprising SEQ ID NO:2.

9. An isolated IL-1β binding molecule that is capable of inhibiting the binding of IL-1β to the IL-1β receptor to the same extent as an IL-1β binding molecule comprising a heavy chain variable domain comprising SEQ ID NO:1 and a light chain variable domain comprising SEQ ID NO:2.

10. An isolated IL-1β binding molecule that is capable of inhibiting the binding of IL-1β to the IL-1β receptor to the same extent as an IL-1β binding molecule comprising a heavy chain variable domain comprising the three CDRs of SEQ ID NO:1 and a light chain variable domain comprising the three CDRs of SEQ ID NO:2.

11. The isolated IL-1β binding molecule of any one of claims 1-10, wherein said IL-1β binding molecule is a human antibody.

12. A composition comprising the isolated IL-1β binding molecule of any one of claims 1-10 and a pharmaceutically acceptable diluent, excipient, carrier or mixture thereof.

13. A composition comprising the isolated IL-1β binding molecule of claim 11 and a pharmaceutically acceptable diluent, excipient, carrier or mixture thereof.

* * * * *